(12) United States Patent
Singer et al.

(10) Patent No.: US 9,089,491 B2
(45) Date of Patent: *Jul. 28, 2015

(54) COSMETIC COMPOSITIONS WITH A SPONGY TEXTURE

(75) Inventors: Jim Mitchell Singer, South Orange, NJ (US); Anita Chon Tong, Garwood, NJ (US)

(73) Assignee: L'ORÉAL (FR)

( * ) Notice: Subject to any disclaimer, the term of this patent is extended or adjusted under 35 U.S.C. 154(b) by 570 days.

This patent is subject to a terminal disclaimer.

(21) Appl. No.: 12/624,464

(22) Filed: Nov. 24, 2009

(65) Prior Publication Data

US 2010/0129307 A1    May 27, 2010

Related U.S. Application Data

(60) Provisional application No. 61/118,032, filed on Nov. 26, 2008.

(51) Int. Cl.
  *A61K 8/25* (2006.01)
  *A61K 8/81* (2006.01)
  *A61Q 5/06* (2006.01)

(52) U.S. Cl.
  CPC .................. *A61K 8/25* (2013.01); *A61K 8/8152* (2013.01); *A61Q 5/06* (2013.01)

(58) Field of Classification Search
  CPC .......... A61K 8/25; A61K 8/8152; A61Q 5/06
  USPC .............................. 424/70.13, 70.11, 70.1, 401
  See application file for complete search history.

(56) References Cited

U.S. PATENT DOCUMENTS

| | | | |
|---|---|---|---|
| 3,915,921 A | | 10/1975 | Schlatzer, Jr. et al. |
| 4,436,862 A | * | 3/1984 | Tetenbaum et al. ............ 524/445 |
| 4,509,949 A | | 4/1985 | Huang et al. |
| 5,879,669 A | | 3/1999 | Clausen et al. |
| 5,882,662 A | | 3/1999 | Pahlck et al. |
| 6,524,563 B1 | | 2/2003 | Wire et al. |
| 2002/0034486 A1 | | 3/2002 | Midha et al. |
| 2004/0170575 A1 | | 9/2004 | Belli et al. |
| 2004/0175286 A1 | * | 9/2004 | Hammond ...................... 419/37 |
| 2005/0158000 A1 | * | 7/2005 | Szum et al. .................... 385/128 |
| 2005/0208412 A1 | * | 9/2005 | Iwazaki et al. ............. 430/110.1 |
| 2005/0244442 A1 | * | 11/2005 | Sabino et al. ................. 424/401 |
| 2005/0271595 A1 | * | 12/2005 | Brown ......................... 424/10.1 |

FOREIGN PATENT DOCUMENTS

| | | |
|---|---|---|
| DE | 0173109 | 3/1986 |
| DE | 10358780 | 7/2005 |
| EP | 1235547 | 5/2001 |
| EP | 1267802 | 10/2001 |
| EP | 1267805 | 10/2001 |
| EP | 1 402 877 | 3/2004 |
| EP | 1 402 877 A1 * | 3/2004 |
| EP | 1402877 A1 | 3/2004 |
| EP | 1722756 | 7/2005 |
| EP | 2108358 A1 | 10/2009 |
| EP | 2111847 A1 | 10/2009 |
| WO | WO 01/30310 | 5/2001 |
| WO | 0174311 A2 | 10/2001 |
| WO | WO 01/74310 | 10/2001 |
| WO | WO 01/74311 | 10/2001 |
| WO | WO 01/74311 A2 * | 10/2001 |
| WO | WO 01/74312 | 10/2001 |
| WO | WO 2004/043865 | 5/2004 |
| WO | 2005025526 A1 | 3/2005 |
| WO | WO 2005/025526 | 3/2005 |
| WO | WO 2005/025526 A1 * | 3/2005 |
| WO | WO 2005/060926 | 7/2005 |
| WO | 2006018065 A1 | 2/2006 |
| WO | WO 2006/018065 | 2/2006 |
| WO | WO 2006/053333 | 5/2006 |

OTHER PUBLICATIONS

European Search Report dated Mar. 26, 2010 as received in corresponding European application No. 09306133.1.

European Examination Report for Application No. 09306133.1 dated Jan. 23, 2013.

M.R. Porter, Handbook of Surfactants, 1991, pp. 116-178, Blackie & Son Editor (Glasgow and London).

Jordi Labanda, Josep Sabate, Joan Llorens, Rheology changes of Laponite aqueous dispersions due to the addition of sodium polyacrylates of different molecular weights, Colloids and Surfaces A, Physicochem. Eng. Aspects 301, ScienceDirect (2007), pp. 8-15, Elsevier, available online Jan. 14, 2007, www.sciencedirect.www.

A. Mourchid and P. Levitz, Long-term gelation of laponite aqueous dispersions, Rapid Communications, May 1998, pp. R4887-R4890, vol. 57, No. 5, The American Physical Society.

Jordi Labanda, Joan Llorens, Influence of sodium polyacylate on the rheology of aqueous Laponite dispersions, Journal of Colloids and Interface Science 289 (2005) pp. 86-93, ScienceDirect, Elsevier, available on line Apr. 27, 2005 www.sciencedirect.com.

Daniel Bonn, Hamid Kellay, Hajime Tanaka, Gerard Wegdam and Jacques Meunier, Laponite: What is the Difference between a Gel and a Glass?, ACS Publications, Sep. 16, 1999, The American Chemical Society, http://pubs.acs.org/cgi-bin/abstract.cgi/langd5/1999/15/i22/abs/la990167+.html.

* cited by examiner

*Primary Examiner* — Blessing M Fubara

(74) *Attorney, Agent, or Firm* — Lerner, David, Littenberg, Krumholz & Mentlik, LLP

(57) ABSTRACT

The present invention concerns a cosmetic composition comprising:
(a) at least one silicate clay,
(b) at least one polymeric rheology modifier, and
(c) at least one solvent.
Such a composition is useful for treating keratinous material, and in particular for styling and/or fixing the hair.

17 Claims, 1 Drawing Sheet

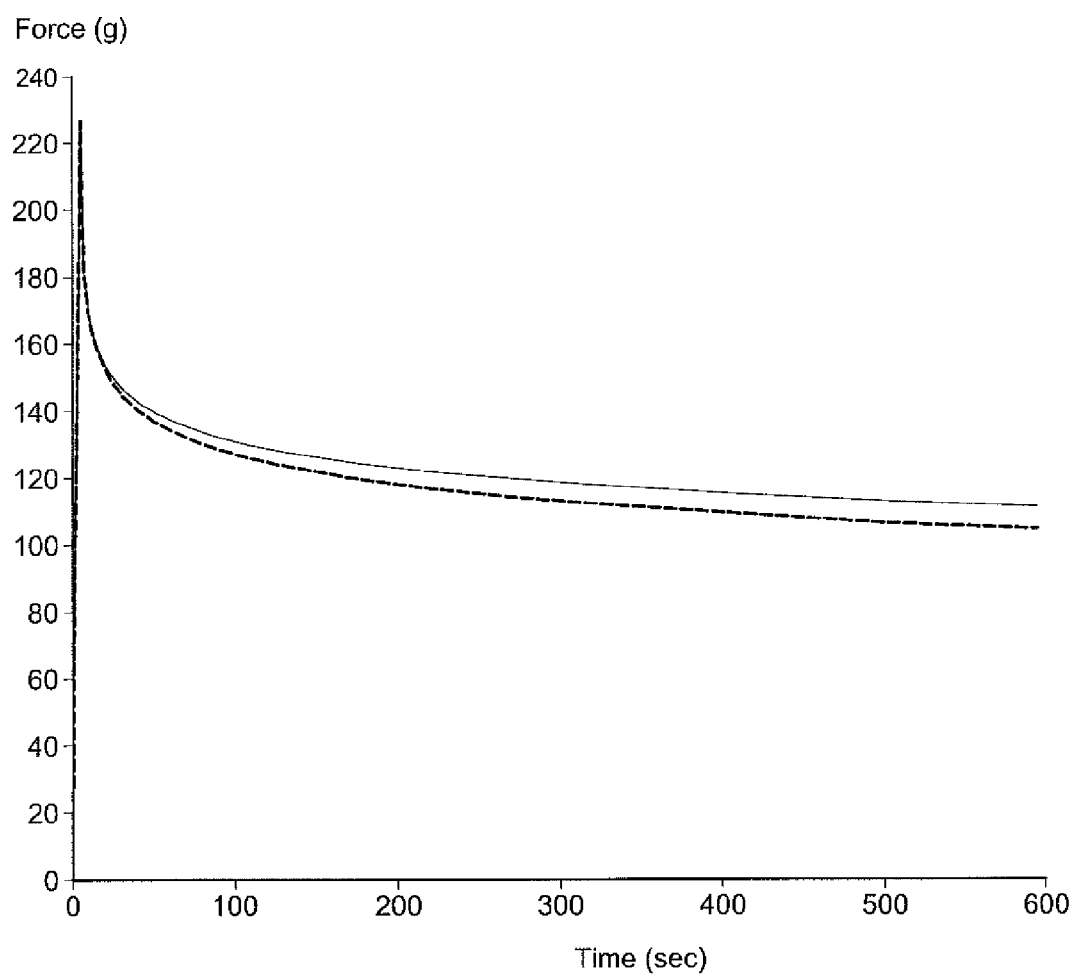

COSMETIC COMPOSITIONS WITH A SPONGY TEXTURE

CROSS-REFERENCE TO RELATED APPLICATION

This application claims the benefit of the filing date of U.S. Provisional Application No. 61/118,032, filed Nov. 26, 2008, the contents of which are incorporated by reference.

BACKGROUND OF THE INVENTION

Various hair cosmetic compositions differ in their efficacies based on the needs and desires of the consumer. Patrons of cosmetic products actively seek out multi-functional, new products which are pleasing to the senses, both on application and in use, and which have innovative, interesting and/or pleasing textures, preferably without any sacrifice to functional performance. One important functional element of such compositions is their ability to hold or set hair in place. Many consumers seek hair styling products which would give a medium hold that adds volume and bounce to the hair and at the same time, provides a very natural or matte looking finish. The resulting feel and texture of the product during the application process, in addition to the feel of the hair after the application are also important elements of such commodities. While different technologies and products exist that have these qualities, there is still a need for improvement in these areas.

Hair styling compositions on the cosmetic market for shaping and/or maintaining the hairstyle appear in various forms. They can range anywhere from solutions, foams, gels, creams, waxes, serums, to aerosols and can provide many different types of finishes to the hair, ranging from silky to matte and polished to edgy. However, these conventional cosmetic compositions have failed to provide the consumer with new and innovative formulations from both a sensory and functionality perspective.

Thus, the object of this invention is related to a composition and process of treating the hair based on a hair styling composition with a unique, spongy texture that facilitates a flexible hold with added bounce and volume to hair and at the same time produces a textured look and feel to the hair. Additionally, the inventive composition can provide reshapeable properties to the hair.

Another object of the invention is to provide a composition with a unique texture that is appealing to the consumer, and which imparts cosmetic and personal care benefits to the surface of hair or skin such as coverage, texture, feel and aesthetic effects.

BRIEF SUMMARY OF THE INVENTION

It has surprisingly been found that cosmetic compositions having a unique texture may be formulated with the use of certain types of clays in combination with polymeric rheology modifiers and a solvent such as for example water.

Thus, the present invention is directed to cosmetic composition, containing:
(a) at least one silicate clay,
(b) at least one polymeric rheology modifier, and
(c) at least one solvent.

Preferably, the composition of the present invention is a hair styling composition.

The cosmetic composition of the present invention exhibits an elastic behavior. Furthermore, such a composition, after application to the hair, provides a medium hair styling hold with a soft and textured feel to the hair.

The present invention is also directed to a method for styling a keratinous material, comprising the step of applying onto the keratinous material a composition as described herein.

According to a first preferred embodiment, the composition of the present invention further comprises at least one wax.

According to a second preferred embodiment, the composition of the present invention further comprises at least one fixative polymer.

According to a particularly preferred embodiment, the composition of the present invention comprises at least one wax and at least one fixative polymer.

BRIEF DESCRIPTION OF THE DRAWING

FIG. 1 shows the elastic behavior of the inventive composition as measured by a texture analyzer in a penetrometry study.

DETAILED DESCRIPTION

Other than in the operating examples, or where otherwise indicated, all numbers expressing quantities of ingredients and/or ratios of ingredients are to be understood as being modified in all instances by the term "about".

The cosmetic compositions and methods of the present invention can comprise, consist of, or consist essentially of the essential elements of the invention described herein, as well as any additional or optional ingredients or components described herein or any otherwise useful ingredients found in personal care compositions intended for application to keratinous materials.

The present invention also relates to compositions for application onto hair such as styling waxes, pomades, creams, mousses, hair masques, and styling gels. The inventive compositions may be utilized in leave-on conditioners, permanent waving compositions, hair care products, hair treatment products, and hair styling products.

The present invention may also be utilized in other personal care compositions such as body washes and deodorants, skin care, sun care, lip care, and facial care. In addition, the inventive compositions may be used in make up products such as foundation, powders, mascara, and lipsticks.

More specifically, the compositions according to the invention can be used in the following applications: a product for caring for, treating or protecting keratinous substances and in particular the skin of the face or body, including the scalp, such as a care (day, night or moisturizing) composition for the face or body; an anti-wrinkle or anti-age composition for the face; a mortifying composition for the face; a composition for irritated skin; a make-up-removing composition; or an optionally aftersun, in particular moisturizing, body milk; of a sun protection, artificial tanning (self-tanning) or aftersun care composition; of a hair composition and in particular a cream or a gel for protecting from the sun; a composition for caring for the scalp, in particular a composition for combating hair loss or for promoting hair regrowth; or an antiparasitic shampoo; of a product for making up keratinous substances, such as a foundation, a tinted cream, a blusher, an eyeshadow, a loose or compact powder, a concealer stick, a cover stick, a lipstick or a lipcare product; or a nail varnish, a nail care product, a mascara, a treating mascara or an eyeliner.

The compositions according to the invention find a preferred application as composition for caring for keratinous substances, in particular the hair, and particularly as composition for styling the hair.

It is to be understood that both the foregoing general description and the following detailed description are exemplary and explanatory only, and are not restrictive of the invention.

The term "elastic behavior" as used herein refers to the composition exhibiting a minimum resistance to deformation of 50 g of force after 10 minutes of penetration by a 20 mm cylindrical metal probe.

Preferably, the composition of the present invention exhibits a minimum resistance to deformation of about 100 g of force after 10 minutes of penetration by a 20 mm cylindrical metal probe.

The minimum resistance to deformation as characterized above, and in the rest of the present application, is measured on a 6 mm sample, using a Texture Analyzer TA.XT from the company Stable Micro Systems, at a penetration rate of 1 mm/s.

The term "hair styling" as used herein refers to styling or fixing hair into a desired configuration, such as imparting a style or temporary curl or set (straight or curly) to human hair and retaining or maintaining (grooming, restyling) a desired set or curl configuration.

The term "hair styling composition", encompasses products that are applied to wet, dry or semi-dry hair before, during or after configuring the hair into the shape (curly or straight) desired, without limitation as to the form of the product.

The terms hair "styling" and hair "fixative" agents as used herein, refer collectively to hair styling agents that are hair fixatives and film formers and which are topically applied to the hair to actively contribute to the ease of styling and/or holding of the hair or of a section of the hair, and to maintain the reshapability of the hair or of section of the hair. Therefore, the present invention on hair styling compositions can include hair styling, hair fixative, and hair grooming products that conventionally are applied to wet or dry or semi-dry hair in the form of waxes, gels, rinses, emulsions (oil-in-water, water-in-oil or multiphase emulsions), such as creams, pomades, mousses, foams, shampoos, solids, such as sticks, semisolids and the like, or are applied from a hair styling aid having the hair styling composition impregnated therein or coated thereon, to leave the hair styling agent in contact with the hair for some period until removed, as for example by washing.

The term "medium hold" as used herein refers to imparting a styling or hold to the hair or to a section of the hair without firmly styling the hair, when at the same time maintaining the finished hair style or hair styling for long hours, with the possibility of restyling or refixing or reshaping the hair simply by combing it with fingers or a brush.

Such a medium hold should be long lasting, so that the hairstyle should retain or hold a desired shape or configuration until water, heat, time and/or physical contact destroys the desired shape or configuration.

The term "reshapeable" as used herein means to provide a hair styling or hair style and/or hold that can be restored or modified without the use of water or of additional styling composition and without application of heat. Additional heat and/or styling composition(s), even if not necessary, may be nevertheless be used to improve the reshapeability, for example if hair becomes unduly wet or dirty, is excessively combed, brushed or manipulated, washed, or when hair is to be dramatically restyled.

As a further advantage, the compositions in accordance with the invention should be reshapeable, as judged by a professional hair stylist of ordinary skill, for at least 4 hours and up to 24 hours or more after initial application of an efficient amount of composition onto the hair. Preferably, in order to restore or modify the hairstyle in case of "drooping" or loss of styling (dishevelment), no new materials, such as water or any fixing agent, and no heat are required. Other terms, which may be synonymous with reshapeable, include repositionable, remoldable, restyleable, rearrangeable, and remodellable.

The composition of the present invention may be in any form. As a preferred embodiment, the composition is under the form of a solid or a semi-solid, such as a paste, a pomade, a cream or a wax.

The composition can be in particular a molded composition or cast as a stick or a dish.

The composition of the invention may be transparent or clear, including for example, a composition without pigments.

The Silicate Clay(s):

The composition of the present invention comprises at least one silicate clay.

Preferred silicate clays are those containing at least one cation which may be chosen from calcium, magnesium, aluminium, sodium, potassium, and lithium cations, and mixtures thereof.

Non-limiting examples of such products include smectite clays such as montmorillonites, hectorites, bentonites, beidellites, saponites, vermiculites, stevensite, and chlorites.

One preferred embodiment of the present invention includes compositions which comprise at least one synthetic silicate clay, most preferably lithium magnesium sodium silicate, commercially available from Rockwood under the tradename Laponite®.

Other preferred examples of silicate clays which may be used in the present invention are chosen from lithium magnesium silicate, aluminum calcium sodium silicate, calcium magnesium silicate, sodium magnesium silicate, calcium aluminum borosilicate, magnesium aluminum silicate, sodium potassium aluminum silicate, and sodium silver aluminum silicate.

The at least one clay is present in the compositions of the present invention in an amount of from 0.1% to 10% by weight, preferably in an amount of from 0.5% to 7%, preferably in an amount of from 1% to 5% by weight, based on the total weight of the composition.

The Polymeric Rheology Modifier(s):

For the purposes of the present invention, the term "rheology modifier" means any compound capable of increasing the viscosity of the composition.

The rheology modifier can be chosen from associative and non associative polymeric rheology modifiers. As used herein, the term "associative polymer" refers to a polymer comprising in its chemical structure at least one hydrophilic part, and at least one hydrophobic part.

The non associative polymeric rheology modifiers useful in the present invention include in particular: cellulose and its derivatives, such as for example hydroxyethylcellulose, hydroxypropylcellulose, and carboxymethylcellulose; guar gum and its derivatives, such as hydroxypropylguar; gums of microbial origin, such as xanthan gum and scleroglucan gum; and synthetic polymeric thickeners such as in particular crosslinked homopolymers of acrylic acid, methacrylic acid, or one of their simple esters, and crosslinked homopolymers of acrylamidopropanesulphonic acid.

Particularly preferred are homopolymers of acrylic acid, methacrylic acid, or one of their simple esters crosslinked with an allyl ether, such as in particular an allyl ether of pentaerythritol, an allyl ether of sucrose, or an allyl ether of propylene.

Particularly preferred are carbomer polymers (homopolymers of acrylic acid crosslinked with an allyl ether, such as in particular an allyl ether of pentaerythritol, an allyl ether of sucrose, or an allyl ether of propylene), such as the products sold under the trade name Carbopol by the company Lubrizol. A particularly preferred commercial product is Carbopol Ultrez 10 Polymer® from Lubrizol.

Associative polymeric rheology modifiers that may be used according to the present invention can be chosen from anionic, cationic, amphoteric, and nonionic associative polymers.

Preferred anionic associative polymers are the following:

(I) anionic associative polymers comprising at least one hydrophilic, unit and at least one fatty-chain allyl ether unit, for example anionic associative polymers whose hydrophilic unit comprises at least one ethylenic unsaturated anionic monomer, in particular at least one acid chosen from vinylcarboxylic acid such as acrylic acid, methacrylic acid, and mixtures thereof, and the fatty-chain allyl ether unit of which corresponds to the monomer of formula (I) below:

$$CH_2=CR'CH_2OB_nR \qquad (I)$$

in which R' is chosen from a hydrogen atom and a methyl group; B is an ethyleneoxy radical; n is chosen from an integer ranging from 0 to 100; and R is a hydrocarbon-based radical chosen from alkyl, arylalkyl, aryl, alkylaryl, and cycloalkyl radicals, having from 8 to 30 carbon atoms, preferably from 10 to 24 carbon atoms, and more preferably from 12 to 18 carbon atoms. A preferred unit of formula (I) is a unit in which R' is a hydrogen atom, n is equal to 10, and R is a stearyl (C18) radical.

Anionic amphiphilic polymers of this type are, for example, described and prepared according to an emulsion polymerization process in patent EP 0 216 479.

Among these types of fatty chain anionic associative polymers, preferred polymers are those formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate, and methylenebisacrylamide.

Among the latest polymers, preferred polymers are chosen from crosslinked terpolymers of methacrylic acid, of ethyl acrylate, and of polyethylene glycol (10 EO) stearyl alcohol ether (Steareth-10), for example, those sold by the company Allied Colloids under the names Salcare SC 80 and Salcare SC 90, which are aqueous 30% emulsions of a crosslinked terpolymer of methacrylic acid, of ethyl acrylate and of steareth-10 alkyl ether (40/50/10).

(II) anionic associative polymers comprising at least one hydrophilic unit of an unsaturated olefinic carboxylic acid, and at least one hydrophobic unit of an unsaturated carboxylic acid (C10-C30)alkyl ester.

These polymers may be chosen from those in which the hydrophilic unit of an unsaturated olefinic carboxylic acid corresponds to the monomer of formula (II) below:

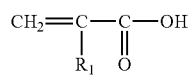

in which $R_1$ is chosen from hydrogen, methyl, and ethyl, that is to say acrylic acid, methacrylic acid, and ethacrylic acid units, and in which the hydrophobic unit of an unsaturated carboxylic acid (C10-C30)alkyl ester corresponds to the monomer of formula (III) below:

in which $R_2$ is chosen from hydrogen, methyl, and ethyl, that is to say acrylate, methacrylate, and ethacrylate units, and preferably $R_2$ is chosen from hydrogen (that is to say acrylate units), and methyl (that is to say methacrylate units), and $R_3$ is a C10-C30, and preferably a C12-C22 alkyl radical.

(C10-C30) alkyl esters of unsaturated carboxylic acids include, for example, lauryl acrylate, stearyl acrylate, decyl acrylate, isodecyl acrylate, dodecyl acrylate, and corresponding methacrylates, such as lauryl methacrylate, stearyl methacrylate, decyl methacrylate, isodecyl methacrylate, and dodecyl methacrylate.

Anionic polymers of this type are described and prepared, for example, in U.S. Pat. Nos. 3,915,921 and 4,509,949.

Among the anionic associative polymers of this type, those that can preferably be used include polymers formed from a monomer mixture comprising:
(i) acrylic acid as main monomer;
(ii) at least one ester of formula (III) described above in which $R_2$ is chosen from hydrogen and methyl, and $R_3$ is chosen from alkyl radicals containing from 12 to 22 carbon atoms; and
(iii) and at least one crosslinking agent, which may be chosen from well-known copolymerizable polyethylenic unsaturated monomers, for instance allyl ethers, diallyl phthalate, allyl (meth)acrylate, divinylbenzene, (poly)ethylene glycol dimethacrylate, and methylenebisacrylamide.

Among fatty-chain anionic associative polymers of this type, those that can be preferably used are those comprising from 60% to 95% by weight of acrylic acid as hydrophilic unit, 4% to 40% by weight of C10-C30 alkyl acrylate as hydrophobic unit, and 0% to 6% by weight of crosslinking polymerizable monomer; or those comprising from 96% to 98% by weight of acrylic acid as hydrophilic unit, 1% to 4% by weight of C10-C30 alkyl acrylate as hydrophobic unit, and 0.1% to 0.6% by weight of crosslinking polymerizable monomer such as those described above.

Among the above-mentioned polymers, examples of preferred commercial products include the products sold by the company Lubrizol under the trade names Pemulen TR-1, Pemulen TR-2, Carbopol Ultrez 20 and 21, and the product sold by the company SEPPIC under the name Coatex SX. In at least one particularly preferred embodiment, the polymer is Pemulen TR-1 (acrylates/C10-30 alkyl acrylate crosspolymer).

(III) maleic anhydride/C30-C38 alpha-olefin/alkyl maleate terpolymers, such as the product (maleic anhydride/C 30-C38 alpha-olefin/isopropyl maleate copolymer) sold under the name Performa V 1608 by the company Newphase Technologies;

(IV) acrylic terpolymers comprising:
(a) 20% to 70% by weight of a carboxylic acid containing [alpha],[beta]-monoethylenic unsaturation;
(b) 20% to 80% by weight of a non-surfactant monomer containing [alpha],[beta]-monoethylenic unsaturation and being other than (a);
(c) 0.5% to 60% by weight of a non-ionic mono-urethane which is the product of reaction of a monohydric surfactant with a monoisocyanate containing monoethylenic unsaturation.

A preferred example of such polymer is a methacrylic acid/methyl acrylate/behenyl alcohol dimethyl-meta-isopropenylbenzylisocyanate ethoxylated (40 EO) terpolymer, described as an aqueous 25% dispersion in application EP-A-0173109.

(V) copolymers comprising among their monomers a carboxylic acid containing alpha, beta-monoethylenic unsaturation and an ester of a carboxylic acid containing alpha,beta-monoethylenic unsaturation and of an oxyalkylenated fatty alcohol.

These compounds preferably further comprise as a monomer at least one ester of a carboxylic acid containing [alpha], [beta]-monoethylenic unsaturation and of a C1-C4 alcohol.

A non-limiting example of a compound of this type is Aculyn 22 sold by the company Rohm and Haas, which is a methacrylic acid/ethyl acrylate/stearyl methacrylate oxyalkylenated terpolymer.

Cationic associative polymers may include, but are not limited to:
(I) cationic associative polyurethanes, which can be formed from diisocyanates and from various compounds with functions containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes" according to the present invention" encompasses these three types of polymer, namely polyurethanes per se, polyureas and polythioureas, and also copolymers thereof. Example of diisocyanates useful in the preparation of the cationic associative polyurethanes include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate.
(II) quaternized cellulose derivatives.

The quaternized cellulose derivatives include, in particular:
quaternized celluloses modified with groups comprising at least one fatty chain, such as alkyl, arylalkyl, and alkylaryl groups comprising at least 8 carbon atoms, and mixtures thereof; and
quaternized hydroxyethylcelluloses modified with groups comprising at least one fatty chain, such as alkyl, arylalkyl, and alkylaryl groups comprising at least 8 carbon atoms, and mixtures thereof.

The alkyl radicals borne by the above quaternized celluloses or hydroxyethylcelluloses comprise preferably from 8 to 30 carbon atoms. The aryl radicals may in particular be chosen from phenyl, benzyl, naphthyl, and anthryl groups.

Examples of quaternized alkylhydroxyethylcelluloses containing C8-C30 fatty chains include, for instance, the products Quatrisoft LM 200, Quatrisoft LM-X 529-18-A, Quatrisoft LM-X 529-18B (C12 alkyl), and Quatrisoft LM-X 529-8 (C18 alkyl) sold by the company Amerchol, and the products Crodacel QM, Crodacel QL (C12 alkyl) and Crodacel QS (C18 alkyl) sold by the company Croda.

(III) polyacrylates containing non-cyclic amine side groups.

Such polyacrylates, which may be quaternized or non-quaternized, comprise hydrophobic groups, such as for example steareth 20 hydrophobic groups (polyoxyethylenated (20) stearyl alcohol).

Examples that may be mentioned of polyacrylates comprising amine side chains include the polymers 8781-121B or 9492-103 provided by the company National Starch.

The amphoteric associative polymers may be chosen, in particular, from those comprising. C8-C30 fatty chains and comprising at least one non-cyclic cationic unit. The amphoteric associative polymers that are particularly preferred according to the present invention are chosen from acrylic acid/(meth)acrylamidopropyltrimethyl-ammonium chloride/stearyl methacrylate terpolymers.

The nonionic associative polymers that may be used according to the present invention may be chosen from:
(I) celluloses modified with groups comprising at least one fatty chain;
Example of Such Celluloses are:
hydroxyethylcelluloses modified with groups comprising at least one fatty chain, such as alkyl, arylalkyl, and alkylaryl groups, and mixtures thereof, and in which the alkyl groups are, preferably, C8-C22 alkyl groups; examples of commercially available products are the product Natrosol Plus Grade 330 CS (C16 alkyls) sold by the company Aqualon, and the product Bermocoll EHM 100 sold by the company Berol Nobel,
the celluloses modified with alkylphenyl polyalkylene glycol ether groups, such as the product Amercell Polymer HM-1500 (nonylphenyl polyethylene glycol (15) ether) sold by the company Amerchol.
(II) hydroxypropyl guars modified with groups comprising at least one fatty chain, such as the product Esaflor HM 22 (C22 alkyl chain) sold by the company Lamberti, and the products RE210-18 (C14 alkyl chain) and RE205-1 (C20 alkyl chain) sold by the company Rhone-Poulenc.
(III) copolymers of vinylpyrrolidone and of fatty-chain hydrophobic monomers; for example:
the products Antaron V216 or Ganex V216 (vinylpyrrolidone/hexa-decene copolymer) sold by the company I.S.P.
the products Antaron V220 or Ganex V220 (vinylpyrrolidone/eicosene copolymer) sold by the company I.S.P.
(IV) copolymers of C1-C6 alkyl methacrylates or acrylates and of amphiphilic monomers comprising at least one fatty chain, for example, the oxyethylenated methyl acrylate/stearyl acrylate copolymer sold by the company Goldschmidt under the name Antil 208.
(V) copolymers of hydrophilic methacrylates or acrylates and of hydrophobic monomers comprising at least one fatty chain, such as for example, the polyethylene glycol methacrylate/lauryl methacrylate copolymer.
(VI) polyurethane polyethers comprising in their chain both hydrophilic blocks usually of polyoxyethylenated nature and hydrophobic blocks which may be aliphatic sequences alone and/or cycloaliphatic and/or aromatic sequences.
(VII) polymers with an aminoplast ether skeleton containing at least one fatty chain, such as the Pure Thix compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. For example, it is possible for at least one pendent chain to be included. Furthermore, the polymer may comprise a hydrocarbon-based chain at one end or at both ends of a hydrophilic block.

The polyurethane polyethers may be multiblock, for example, in triblock form. Hydrophobic blocks may be at each end of the chain (for example: triblock copolymer with a hydrophilic central block) or distributed both at the ends and in the chain (for example: multiblock copolymer). These polymers may also be chosen from graft polymers and starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers may comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

Examples of nonionic fatty-chain polyurethane polyethers that may be used include Rheolate 205 containing a urea function, sold by the company Rheox, Rheolate 208, 204, and 212, and also Acrysol RM 184.

Polyurethanes may also be chosen, for example, from the product Elfacos T210 containing a C12-14 alkyl chain, and the product Elfacos T212 containing a C 18 alkyl chain, from Akzo.

The product DW 1206B from Rohm and Haas containing a C20 alkyl chain and a urethane linkage, sold at a solids content of 20% in water, may also be used.

It is also possible to use solutions or dispersions of these polymers, for example, in water or in aqueous-alcoholic medium. Examples of such polymers include, but are not limited to, Rheolate 255, Rheolate 278 and Rheolate 244 sold by the company Rheox, and the products DW 1206F and DW 1206J sold by the company Rohm and Haas.

In at least one embodiment, the polyurethane polyether may be chosen from those that may be obtained by polycondensation of at least three compounds comprising of: (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm and Haas under the names Aculyn 44 and Aculyn 46 [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%)].

The at least one rheology modifier is preferably chosen from associative and non-associative, crosslinked and not crosslinked homopolymers and copolymers of acrylic acid, and in particular: acrylates/C10-30 alkyl acrylate crosspolymer, acrylates/C10-20 alkyl acrylate crosspolymer, acrylates/beheneth-25 methacrylate copolymer, acrylates/vinyl neodecanoate crosspolymer, sodium acrylates/vinyl isodecanoate crosspolymer, acrylates crosspolymer, carbomer, and mixtures thereof.

The at least one rheology modifier is more preferably chosen from acrylates/C10-30 alkyl acrylate crosspolymer (commercially available from Lubrizol under the trade names Pemulen TR-1 Polymer®, Pemulen TR-2 Polymer®), carbomer (commercially available from Lubrizol under the trade name Carbopol Ultrez 10 Polymer®) and mixtures thereof.

The at least one rheology modifier may be predispersed in a wetting agent prior to use.

The at least one rheology modifier may also be used in pre-neutralized condition. Any conventional neutralizing agent may be used.

The at least one rheology modifier can be present in the compositions of the present invention in an amount of from 0.05% to 5% by weight, preferably from 0.1% to 2% by weight, more preferably from 0.2% to 1% by weight, even more preferably from 0.3% to 0.8% by weight, based on the total weight of the composition.

Solvent

The at least one solvent may be chosen from water, organic solvents and mixtures thereof. By way of organic solvent, suitable examples include C1-C4 lower alkanols, such as ethanol and isopropanol; polyols and polyol ethers such as 2-butoxyethanol, propylene glycol, propylene glycol monomethyl ether, diethylene glycol monoethyl ether and monomethyl ether; and aromatic alcohols such as benzyl alcohol or phenoxyethanol, and mixtures thereof. Other examples of solvents for use in the present invention are hexyleneglycol and dipropylene glycol, and mixtures thereof.

In one preferred embodiment of the present invention, the solvent is water.

In another preferred embodiment of the present invention, the solvent is a mixture of water and of an organic solvent as described above.

In another embodiment of the present invention, the organic solvent is a polar organic solvent.

Wax

The compositions of the present invention may also contain at least one wax to modify the viscosity, feel or stability. Waxes are lower-melting organic mixtures or compounds of high molecular weight, which are solid at room temperature. They are generally similar in composition to fats and oils except that they contain no glycerides. They can be chosen in particular from hydrocarbons, and esters of fatty acids or fatty alcohols.

For the purposes of the invention, the waxes are those generally used in cosmetics and dermatology. Waxes useful in the present invention are selected from the group consisting of animal waxes, vegetable waxes, mineral waxes, natural waxes, synthetic waxes, petroleum waxes, ethylenic polymers, hydrocarbons, silicone waxes, alkyl esters and mixtures thereof.

Examples of waxes of animal origin include beeswaxes, lanolin waxes and Chinese insect waxes.

Examples of waxes of plant origin include rice waxes, carnauba wax, candelilla wax, ouricurry wax, cork fibre waxes, sugar cane waxes, Japan waxes, sumach wax and cotton wax.

Examples of waxes of mineral origin include paraffins, microcrystalline waxes, montan waxes and ozokerites.

Examples of waxes of synthetic origin include polyolefin waxes, e.g., polyethylene waxes, waxes obtained by Fischer Tropsch synthesis, waxy copolymers and their esters, and silicone and fluoro waxes.

Alternatively, hydrogenated oils of animal or plant origin may be used. Examples include hydrogenated jojoba waxes and hydrogenated oils which are obtained by catalytic hydrogenation of fats composed of a C8-C32 linear or nonlinear fatty chain, hydrogenated sunflower oil, hydrogenated castor oil, hydrogenated copra oil, hydrogenated lanolin and hydrogenated palm oils.

The at least one wax is preferably chosen from beeswax, cetyl esters, ozokerite, ouricurry wax, cork fibre wax, sugar cane wax, Japan wax, sumach wax, cotton wax, lanolin wax, rice wax, hydrogenated sunflower oil, hydrogenated castor oil, hydrogenated copra oil, hydrogenated lanolin, hydrogenated palm oil, jojoba wax, and mixtures thereof.

In some embodiments, the composition can contain at least two or at least three waxes.

The wax can be present in the composition of the present invention in an amount generally ranging from 0.1% to 10% by weight, preferably from 1% to 5% by weight, based on the total weight of the composition. The amount of wax phase present in the composition may vary, depending for example on the hardness of the product desired.

Fixative Polymer

The fixative polymers that can be used in the present invention may be chosen from anionic, cationic, amphoteric and non-ionic fixative polymers and mixtures thereof. The fixative polymer may additionally be halogenated, in particular fluorinated.

The fixative polymers can be used in solubilized form or else in the form of dispersions of solid polymer particles (latex or pseudo-latex).

The cationic fixative polymers which can be used according to the present invention can be selected from polymers containing primary, secondary, tertiary and/or quaternary amine groups forming part of the polymer chain or linked directly to it and having a molecular weight of between 500 and approximately 5,000,000 and preferably between 1000 and 3,000,000.

In particular, the cationic fixative polymer can preferably be chosen from polyquaternium-4, polyquaternium-6, polyquaternium-7 polyquaternium-10, polyquaternium-11, polyquaternium-16, polyquaternium-22, polyquaternium-28, polyquaternium-32, guar hydroxypropyltrimonium chloride, and mixtures thereof.

The anionic fixative polymers that are generally used are polymers containing groups derived from carboxylic, sulphonic or phosphoric acid and have a weight-average molecular weight of between approximately 500 and 5,000,000.

The carboxylic groups are provided by unsaturated mono- or dicarboxylic acids monomers such as those corresponding to the formula (IV):

(IV)

in which:
n is an integer from 0 to 10,
$A_1$ denotes a methylene group, optionally connected to the carbon atom of the unsaturated group, or to the neighboring methylene group when n is greater than 1, via a hetero atom such as oxygen or sulphur,
$R_7$ denotes a hydrogen atom or a phenyl or benzyl group,
$R_8$ denotes a hydrogen atom or a lower alkyl or carboxyl group, and
$R_9$ denotes a hydrogen atom, a lower alkyl group or a —$CH_2$—COOH, phenyl or benzyl group.

In the abovementioned formula, a lower alkyl radical preferably denotes a group having 1 to 4 carbon atoms and in particular methyl and ethyl.

The anionic fixative polymers containing carboxylic groups which are preferred according to the invention are:

A) Copolymers of acrylic or methacrylic acid or salts thereof and in particular the products sold under the names VERSICOL E or K by the company Allied Colloid and ULTRAHOLD by the company BASF; and the copolymers of acrylic acid and of acrylamide such as the products sold in the form of their sodium salt under the names RETEN 421, 423 or 425 by the company Hercules, the sodium salts of polyhydroxycarboxylic acids.

B) Copolymers of acrylic or methacrylic acids with a monoethylenic monomer chosen from ethylene, styrene, vinyl esters, acrylic acid esters or methacrylic acid esters. These copolymers can be grafted onto a polyalkylene glycol such as polyethylene glycol and optionally crosslinked. Mention may be made in particular of the copolymers containing an optionally N-alkylated and/or hydroxyalkylated acrylamide unit in their chain sold under the name QUADRAMER by the company American Cyanamid. Mention may also be made of copolymers of acrylic acid and of $C_1$-$C_4$ alkyl methacrylate and terpolymers of vinylpyrrolidone, of (meth)acrylic acid and of (meth)acrylate of $C_1$-$C_{20}$ alkyl, for example lauryl (such as the product sold by the company ISP under the name ACRYLIDONE LM), tert-butyl (LUVIFLEX VBM 70 sold by BASF) or methyl (STEPANHOLD EXTRA sold by Stepan) and methacrylic acid/ethyl acrylate/tert-butyl acrylate terpolymers such as the product sold under the name LUVIMER 100 P by the company BASF.

C) Copolymers derived from crotonic acid such as those containing vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Commercial products falling into this class are the resins 28-29-30, 26-13-14 and 28-13-10 sold by the company National Starch.

D) Copolymers derived from C4-C8 monounsaturated carboxylic acids or anhydrides selected from:
    copolymers comprising:
    (i) one or more maleic, fumaric or itaconic acids or anhydrides and
    (ii) at least one monomer selected from vinyl esters, vinyl ethers, vinyl halides, phenylvinyl derivatives, acrylic acid and its esters, the anhydride functions of these copolymers optionally being monoesterified or monoamidated. Commercially available examples thereof include, but are not limited to, GANTREZ AN or ES and AVANTAGE CP and Aquaflex FX-64 from the company ISP;
    copolymers comprising:
    (i) one or more maleic, citraconic or itaconic anhydrides and
    (ii) one or more monomers selected from allylic or methallylic esters optionally containing one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

E) Polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be selected in particular from:
polyvinylsulphonic acid salts having a weight-average molecular weight ranging from approximately 1000 to approximately 100,000, as well as the copolymers with an unsaturated comonomer such as acrylic or methacrylic acids and their esters, as well as acrylamide or its derivatives, vinyl ethers and vinylpyrrolidone;

polystyrenesulphonic acid salts, the sodium salts having a weight-average molecular weight of about 500,000 and about 100,000, which are sold respectively under the names FLEXAN 500 and FLEXAN 130 by National Starch;

polyacrylamidesulfonic acid salts. One example thereof is polyacrylamidoethylpropanesulphonic acid sold under the name COSMEDIA POLYMER HSP 1180 by Henkel.

Anionic fixative polymers may be also be sulphonated polyesters comprising repeating units representable by the following general formula:

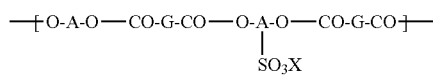

in which A and G represent divalent radicals and X represents an alkali metal, especially sodium or potassium. Among the preferred sulphonated polyesters according to the invention, A represents an arylene radical, especially phenylene, and G represents a linear or branched alkylene radical optionally interrupted by one or more oxygen atoms, or a cycloalkylene radical.

The alkylene radical is preferably, according to the invention, a lower, linear or branched $C_2$-$C_4$ alkylene radical, more preferably an ethylene radical Among these polymers, preference will be given to those marketed under the names AQ 1045, AQ 1350 and AQ 14000 by the company EASTMAN CHEMICAL, more particularly AQ 1350.

According to the invention the anionic fixative polymers are preferably selected from acrylic acid copolymers such as the acrylic acid/ethyl acrylate/N-tert-butylacrylamide terpolymers sold in particular under the name ULTRAHOLD STRONG by the company BASF, copolymers derived from crotonic acid such as the vinyl acetate/vinyl tert-butylbenzoate/crotonic acid terpolymers and the crotonic acid/vinyl acetate/vinyl neododecanoate terpolymers sold in particular under the name RESIN 28-29-30 by the company National Starch, polymers derived from maleic, fumaric or itaconic acids or anhydrides with vinyl esters, vinyl ethers, vinyl halides, phenylvinyl derivatives or acrylic acid and its esters, such as the methyl vinyl ether/maleic anhydride monoesterified copolymers sold, for example, under the name GANTREZ by the company ISP, the copolymers of methacrylic acid and of methyl methacrylate sold under the name EUDRAGIT L by the company Rohm Pharma, the copolymers of methacrylic acid/methyl methacrylate/$C_1$-$C_4$ alkyl acrylate/acrylic acid or $C_1$-$C_4$ hydroxyalkyl methacrylate which are sold in the form of dispersions under the name AMERHOLD DR 25 by the company Amerchol or under the name ACUDYNE 255 by the company Rohm & Haas, the copolymers of methacrylic acid and of ethyl acrylate sold under the name LUVIMER MAEX or MAE by the company BASF and the vinyl acetate/crotonic acid copolymers and the vinyl acetate/crotonic acid copolymers grafted with polyethylene glycol, sold under the name ARISTOFLEX A by the company BASF.

The anionic fixative polymers which are more preferred are selected from the monoesterified methyl vinyl ether/maleic anhydride copolymers sold under the name GANTREZ ES 425 by the company ISP, the acrylic acid/ethyl acrylate/N-tert-butylacrylamide terpolymers sold under the name ULTRAHOLD STRONG by the company BASF, the copolymers of methacrylic acid and of methyl methacrylate sold under the name EUDRAGIT L by the company Rohm Pharma, the vinyl acetate/vinyl tert-butylbenzoate/crotonic acid terpolymers and the crotonic acid/vinyl acetate/vinyl neododecanoate terpolymers sold under the name RESIN 28-29-30 by the company National Starch, the copolymers of methacrylic acid and of ethyl acrylate sold under the name LUVIMER MAEX or MAE by the company BASF and the vinyl pyrrolidone/acrylic acid/lauryl methacrylate terpolymers sold under the name ACRYLIDONE LM by the company ISP.

The amphoteric fixative polymers which can be used in accordance with the invention can be selected from polymers containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers; B and C can also denote a cationic polymer chain containing primary, secondary, tertiary or quaternary amine groups, in which at least one of the amine groups bears a carboxylic or sulphonic group connected via a hydrocarbon radical, or alternatively B and C form part of a chain of a polymer containing an α,β-dicarboxylic ethylene unit in which one of the carboxylic groups has been made to react with a polyamine containing one or more primary or secondary amine groups.

The amphoteric fixative polymers corresponding to the definition given above which are more particularly preferred are selected from the following polymers:

(1) Polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamides and acrylamides.

(2) Polymers containing units derived from:
a) at least one monomer selected from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are selected more particularly from acrylic acid, methacrylic acid, crotonic acid, itaconic acid, maleic acid and fumaric acid and alkyl monoesters, having from 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA name is octylacrylamide/acrylates/butylaminoethyl methacrylate copolymer such as the products sold under the name AMPHOMER or LOVOC-RYL 47 by the company National Starch are particularly used.

(3) crosslinked and alkylated polyamino amides partially or totally derived from polyamino amides of formula (V):

(V)

in which:

$R_{10}$ represents a divalent radical derived from a saturated dicarboxylic acid, a mono- or dicarboxylic aliphatic acid containing an ethylenic double bond, an ester of a lower alkanol having from 1 to 6 carbon atoms and of the abovementioned acids, or a radical derived from the addition of any one of the abovementioned acids to a bis(primary) or bis (secondary) amine, and Z denotes a bis(primary), mono- or bis(secondary) polyalkylene-polyamine radical and preferably represents:

a) in proportions of from 60 to 100 mol %, the radical

(VI)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (VI) above in which x=2 and p=1 and which is derived from ethylenediamine, or the radical derived from piperazine:

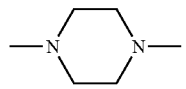

c) in proportions of from 0 to 20 mol %, the —NH—(CH$_2$)$_6$—NH— radical derived from hexamethylenediamine, these polyamino amines being crosslinked by addition of a difunctional crosslinking agent selected from epihalohydrines, diepoxides, dianhydrides and bis-unsaturated derivatives, using from 0.025 to 0.35 mol of crosslinking agent per amine group of the polyamino amide, and acylated by the action of acrylic acid, chloroacetic acid or an alkane sultone, or salts thereof.

The saturated carboxylic acids are preferably selected from acids having from 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the acylating agents are preferably the sodium or potassium salts.

(4) polymers containing zwitterionic units of formula (VII):

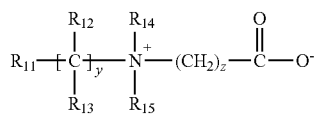
(VII)

in which:

$R_{11}$ denotes a polymerizable unsaturated group such as an acrylate, methacrylate, acrylamide or methacrylamide group, y and z represent an integer ranging from 1 to 3, $R_{12}$ and $R_{13}$ represent a hydrogen atom, methyl, ethyl or propyl, $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate such as the product sold under the name DIAFORMER Z301 by the company Sandoz.

(5) Polymers derived from chitosan containing monomer units corresponding to the following formulae:

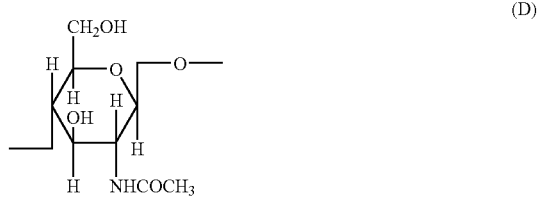
(D)

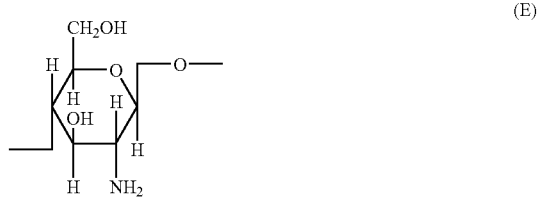
(E)

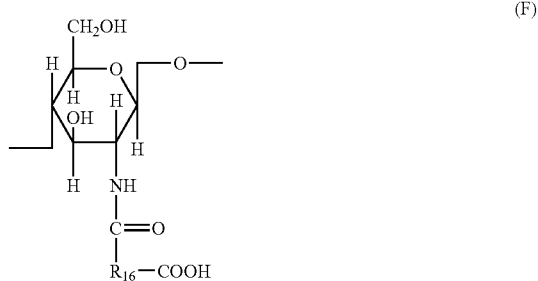
(F)

the unit D being present in a concentration ranging from 0 to 30%, the unit E in a concentration ranging from 5 to 50%, and the unit F in a concentration ranging from 30 to 90%, it being understood that, in this unit F, $R_{16}$ represents a radical of formula:

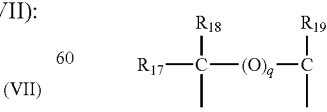

in which, if q=0, $R_{17}$, $R_{18}$ and $R_{19}$ each independently represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being, in this case, a hydrogen atom;

or, if q=1, $R_{17}$, $R_{18}$ and $R_{19}$ each independently represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "EVALSAN" by the company Jan Dekker.

(7) Polymers corresponding to formula (VIII):

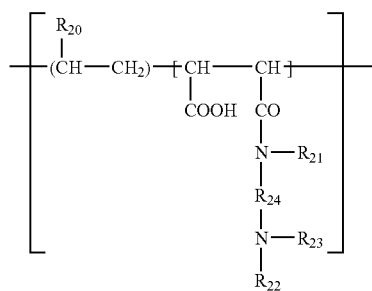

in which:

$R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a C1-C6 lower alkyl radical such as methyl or ethyl, $R_{23}$ denotes a C1-C6 lower alkyl radical such as methyl or ethyl or a radical corresponding to the formula: $-R_{24}-N(R_{22})_2$, $R_{22}$ being as defined above wherein the $R_{22}$ groups can be the same or different, $R_{24}$ representing a $-CH_2-CH_2-$, $-CH_2-CH_2-CH_2-$ or $-CH_2-CH(CH_3)-$ group, and the higher homologues of these radicals containing up to 6 carbon atoms.

(8) Amphoteric polymers of the type -D-X-D-X selected from:

a) polymers obtained by the action of chloroacetic acid or sodium chloroacetate on compounds containing at least one unit of formula:

-D-X-D-X-D- where D denotes a radical

and X denotes the symbol E or E', and E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, from 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) Polymers of formula:

-D-X-D-X— in which D denotes a radical

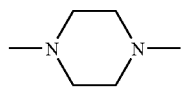

and X denotes the symbol E or E' and at least once E', E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric fixative polymers which are particularly preferred according to the invention are those of family (3), such as the copolymers whose CTFA name is octylacrylamide/acrylates/butylaminoethyl methacrylate copolymer, such as the products sold under the names AMPHOMER, AMPHOMER LV 71 or LOVOCRYL 47 by the company National Starch and those of family (4) such as the copolymer of methyl methacrylate/dimethyl carboxymethylammonio methyl ethylmethacrylate, sold, for example, under the name DIAFORMER Z301 by the company Sandoz.

The anionic or amphoteric fixative polymers can, if necessary, be partially or totally neutralized. The neutralizing agents are, for example, sodium hydroxide, potassium hydroxide, 2-amino-2-methyl-1-propanol, monoethanolamine, triethanolamine or triisopropanolamine and inorganic or organic acids such as hydrochloric acid or citric acid.

The non-ionic fixative polymers useful according to the present invention can be in particular chosen from polyurethanes, and homo and co-polymers of vinyllactam units, such as homo and co-polymers of vinylpyrrolidone.

Particularly preferred fixative polymers are polyvinylpyrrolidone, vinylpyrrolidone/vinyl acetate copolymer, AMP-acrylates/allyl methacrylate copolymer (commercially available from Noveon under the tradename, Fixate G-100), sodium polystyrene sulfonate (commercially available from National Starch under the tradename, Flexan II), vinylpyrrolidone/acrylates/lauryl methacyrlate copolymer (commercially available from ISP under the tradename, Acrylidone LM), acrylates/vinylpyrrolidone copolymer, polyurethane-2 (commercially available from Noveon under the tradename Avalure 405 or 410), polyquaternium-4, polyquaternium-6 polyquaternium-7 polyquaternium-10, polyquaternium-11, polyquaternium-16, polyquaternium-22, polyquaternium-28, polyquaternium-32, guar hydroxypropyltrimonium chloride, and mixtures thereof.

The fixative polymer may be present in the compositions of the present invention at levels ranging from 0.05% to 15% by weight, preferably from 1% to 5% by weight, more preferably from 2% to 3% by weight, based on the total weight of the composition.

The composition(s) of the present invention may further comprise additives different from the ingredients described above, and which can for instance be chosen from (non-exhaustive list): reducing agents, surfactants, antioxidants, sequestering agents, softeners, antifoams, moisturizers, emollients, basifying agents, gelling agents, wetting agents, thickening agents, spreading agents, dispersants, plasticizers, preservatives, sunscreens, direct dyes or oxidation dyes, pigments, mineral fillers, colloidal minerals, nacres, nacreous agents, emulsifying agents, fragrances, peptizers, preserving agents, non-fixing polymers, ceramides, proteins, active agents, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, fatty amides, fatty esters, fatty alcohols, and the like.

In particular, the composition of the present invention can comprise at least one surfactant.

The surfactants that may be used can be chosen from cationic, non-ionic, amphoteric, zwitterionic, anionic surfactants, and mixtures thereof.

Suitable cationic surfactants to be used either alone or in combination in the context of the present invention include ion particular salts of primary, secondary, or tertiary fatty amines, optionally polyoxyalkylenated; quaternary ammonium salts, such as tetraalkylammonium, alkylamidoalkyltrialkylammonium, trialkylbenzylammonium, trialkylhydroxyalkylammonium, or alkylpyridinium chlorides, or bromides; imidazoline derivatives; and amine oxides of cationic nature.

Non-ionic surfactants to be used in the context of the present disclosure include compounds that are well known (for a review thereof, see, for instance, "Handbook of Surfactants" M. R. PORTER, Blackie & Son Editor (Glasgow and London), 1991, pp 116-178). The non-ionic surfactants may be chosen in particular from alcohols, alpha-diols, (C1-C20) alkyl phenols, and polyethoxylated, polypropoxylated, and polyglycerolated fatty acids, having a fatty-chain comprising for example from 8 to 18 carbon atoms, where the number of ethylene oxide or propylene oxide groups may range from 2 to 50, and the number of glycerol groups may range from 2 to 30. Other non-limiting examples include copolymers of ethylene oxide and propylene oxide, condensation products of ethylene oxide and propylene oxide on fatty alcohols; polyethoxylated fatty amides having, for example, from 2 to 30 moles of ethylene oxide; polyglycerolated fatty amides comprising on average from 1 to 5 glycerol groups, such as from 1.5 to 4 glycerol groups; polyethoxylated fatty amines having, for example, from 2 to 30 moles of ethylene oxide; sorbitane fatty acid esters ethoxylated with from 2 to 30 moles of ethylene oxide; sucrose fatty acid esters, polyethylene glycol fatty acid esters, (C6-C24)alkyl polyglucosides, (C6-C24)N-alkyl glucamine derivatives, amine oxides such as (C10-C14)alkyl amine oxides and (C10-C14)N-acyl aminopropylmorpholine oxides.

Nonionic surfactants also include, alkyl, alkyl dimethyl, alkyl amidopropylamine, or bis 2-hydroxy ethyl alkyl amine oxides; alkanolamides; alkyl amides; polyoxyethylene glycol (PEG) of monoglycerides, of sorbitan esters, of branched or linear fatty alcohol ethers, of branched or linear fatty acid ethers, of thioethers; alkyl oxoalcohol PEG; PEG fatty esters; polyoxyethlyene glycol/polyoxpropylene glycol block copolymers; alkyl phenol PEG ethers; alkyl polyglucosides, or polysaccarides; polysiloxane polyethoxylene ethers; and mixtures thereof.

In one preferred embodiment, the composition of the present invention comprises at least one non-ionic surfactant chosen from mixtures of glyceryl stearate & PEG-100 stearate, such as the product commercially available from Croda under the tradename Arlacel 165 FL®.

In another preferred embodiment of the present invention, the composition comprises at least one non-ionic surfactant chosen from (C6-C24) alkyl polyglycosides, such as decyl polyglucoside.

Non-limiting examples of amphoteric and zwitterionic surfactants useful in the composition of the present invention include alkyl, alkyl dimethyl, alkylamido, alkyl amide, alkylamidopropyl, or alkyl dimethylammonium betaines; alkyl amidopropyl or alkyl sulfobetaines; alkyl, alkylampho, or alkylamphocarboxy glycinates; alkyl, or alkyl substituted imidazoline mono or dicarboxylates; sodium salts of alkyl mono- or dicarboxylates; alkyl beta amino acids; alkyl amidopropyl, or alkyl ether hydroxysultaines; alkyl amidopropyl dimethyl ammonia acetates; alkyl ampho mono- or diacetates; alkyl, or alkyl ampho, or alkyl imino dipropionates; alkyl amphopropionates; alkyl beta amino propionic acids; alkyl beta iminodipropionates; branched or n-alkyl dimethylamidopropionates; alkyl carboxylated propionates; alkyl, or methyl alkyl imidazolines; fluorinated alkyl amphoteric mixtures.

Specific examples include cocamidopropyl betaine, lauramidopropyl betaine, coco/oleamidopropyl betaine, lauryl betaine, coco betaine, oleyl betaine, cocamidopropyl hydroxysultaine, tallowamidopropyl hydroxysultaine, dihydroxyethyl tallow glycinate, disodium cocoamphodiacetate, disodium cocoamphodipropionate and mixtures thereof.

Suitable anionic surfactants to be used either alone or in combination in the context of the present disclosure include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, isothienates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl ether carboxylate, lauryl sarcosinate, cocomethyl tauride, and sulfosuccinate half ester amide and mixtures thereof.

The at least one surfactant can be present in the composition in an amount of from 1% to 20% by weight, preferably in an amount of from 2% to 15% by weight, and more preferably in an amount of from 5% to 10.0% by weight, based on the total weight of the composition.

Wetting Agents

The compositions of the present invention may also comprise at least one wetting agent. According to one embodiment, wetting agent(s) may be present when use is made of a rheology modifier that is pre-dispersed by one or more wetting agent(s). The term "wetting agent" means herein any compound which, when introduced into a solution, aids in reducing the surface tension of a solvent or liquid or in reducing the interfacial tension between liquids in order to facilitate spreading and/or to allow better dispersion of other materials in the solution.

The wetting agents, according to the present disclosure, may be selected from:

non-ionic wetting agents, such as fatty acids, fatty alcohols, polyethoxyl or polyglycerol fatty alcohols such as polyethoxylstearyl or cetylstearyl alcohols, esters of fatty acid and saccharose, alkyl glucose esters, in particular, polyoxyethylenated fatty esters of C1-C6 alkyl glucose, C12-15 Alkyl Benzoate and mixtures thereof; and anionic wetting agents, such as C16-C30 fatty acids neutralized by amines, ammonia, or alkali salts, and mixtures thereof.

A particularly preferred wetting agent is C12-15 alkyl benzoate.

The wetting agent can be present in the composition in an amount of from 0.1% to 10% by weight, preferably from 0.5% to 7% by weight, and more preferably from 1.0% to 5.0% by weight, based on the total weight of the composition.

Emulsifying Agents

Emulsifiers or dispersing agents, include, without limitation, any which are compatible with the solvent and ingredients used in the composition of the present invention. The emulsifying agents which can be used according to the invention are those having an HLB of less than 7 and in particular fatty acid esters of polyols such as mono-, di-, tri- or sesquioleates or -stearates of sorbitol or glycerol, laurates of glycerol or polethylene glycol; alkyl or alkoxy dimethicone copolyols having an alkyl or alkoxy chain pendent or at the end of a silicone-based backbone having for example from 6 to 22 carbon atoms. The emulsifying agents may also be those having an HLB greater than 7 such as fatty acid esters of polyethylene glycol (monostearate or monolaurate of polyethylene glycol); esters of fatty acids (stearate, oleate) of sorbitol which are polyoxyethylenated; polyoxy ethylenated alkyl (lauryl, cetyl, stearyl, octyl)ethers and dimethicone copolyols. In general, it is possible to use nonionic or anionic or cationic emulsifiers well known to persons skilled in the art.

The nonionic type emulsifiers are fatty acids or amides of polyalkoxylated and/or polyglycerolated fatty acids; polyoxyethylenated and/or polyoxypropylenated fatty alcohols (i.e., compounds prepared by reacting an aliphatic fatty alcohol such as behenyl or cetyl alcohol with ethylene oxide or propylene oxide or an ethylene oxide/propylene oxide mixture); fatty acid esters of polyols, optionally polyoxyethylenated and/or polyoxypropylenated (i.e., compounds prepared by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture); and polyalkoxylated and/or polyglycerolated alkylphenols; or polyalkoxylated and/or polyglycerolated 1,2- or 1,3-alkanediols; and alkylethers of polyalkoxylated and/or polyglycerolated 1,2- or 1,3-alkanediols or alkenediols, or mixtures thereof.

The polyalkoxylated fatty acids are commercial products, and are principally products sold under the mark "Myrj".

The esters of fatty acids and polyoxyethylenated polyols for which the polyol is sorbitol are known products (Polysorbate and products sold under the mark "Tween").

The polyoxyethylenated fatty alcohols are commercial products and principally those sold under the mark "Brij".

The fatty acids or amides of polyglycerolated fatty acids are also commercial products such as those sold under the mark "Plural" (Gattefosse) or "Drewpol" (Stefan Company).

The emulsifying agents according to the invention can also be anionic surfactants which may have a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms and being able to have a double bond as in the case of oleic acid; the alkaline salts or salts of organic bases of alkyl-sulfuric and alkyl-sulfonic acids having 12 to 18 carbon atoms, of alkyl-aryl-sulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. All these anionic surfactants are well known and many among them are commercial products.

The emulsifying agents according to the invention can also be cationic surfactants such as quaternary ammonium derivatives.

Particularly preferred emulsifying agents are Isoceteth-20, Polysorbate 20, PEG-40 hydrogenated castor oil, oleth-2, laureth-7, cetyl alcohol and glyceryl stearate.

The emulsifying agent may be present in the composition in an amount of from 0.05% to 15% by weight, preferably in an amount of from 0.1% to 10% by weight, and more preferably in an amount of from 0.5% to 6.0% by weight, based on the total weight of the composition.

The present invention further provides a process for treating keratinous materials such as hair, by applying the above-disclosed composition onto the keratinous material. The precise amount of composition to be applied onto the material will depend on the degree of treatment desired.

The present invention also concerns the use of the above-disclosed composition for styling and/or fixing the keratinous material, and in particular the hair.

In one embodiment of the present invention, there is provided a process of making the inventive composition involving combining at least one silicate clay with at least one solvent such as water, then adding at least one polymeric rheology modifier to the mixture, then adding optional ingredients such as waxe(s), surfactant(s) and fixative polymer(s) while mixing and heating until a homogeneous mixture is formed.

According to a particular embodiment, the at least one polymeric rheology modifier is added to the mixture under a pre-dispersed form, using a wetting agent.

Other embodiments of the present invention may be achieved by varying the levels and/or types of silicate clays, rheology modifiers, wetting agents, solvents, waxes, surfactants and fixative polymers in the inventive composition.

The following example further describe and demonstrate embodiments within the scope of the present invention. The example is given solely for the purpose of illustration and are not to be construed as limitations of the present invention, as many variations thereof are possible without departing from the spirit and scope of the invention. All exemplified amounts are concentrations by weight of the total composition, unless otherwise specified.

Example

Hair Styling Composition

The following hair styling composition, containing the ingredients as detailed hereunder, was prepared:

| CHEMICAL NAME | % by weight |
|---|---|
| Lithium magnesium sodium silicate (1) | 2.25 |
| Sodium chloride | 0.02 |
| vinylpyrrolidone/vinyl acetate copolymer (2) | 2.00 |
| Propylene glycol | 3.00 |
| Methylparaben | 0.30 |
| Phenoxyethanol | 0.70 |
| Glyceryl stearate and PEG-100 stearate (3) | 3.75 |
| Cetearyl alcohol | 3.75 |
| Beeswax | 1.75 |
| Cetyl esters (4) | 1.50 |
| Triethanolamine | 0.40 |
| C12-15 alkyl benzoate | 3.20 |
| Acrylates/C10-30 alkyl acrylate crosspolymer (5) | 0.40 |
| Deionized Water | Q.S. to 100 |

(1) sold under the name Laponite by the company Rockwood
(2) sold under the name Luviskol VA 64 Poudre by the company BASF
(3) sold under the name Arlacel 165 FL by the company Croda
(4) sold under the name Crodamol MS-PA by the company Croda
(5) sold under the name Pemulen TR-1 by the company Lubrizol.

Process of Making

The deionized water was placed in a suitably sized beaker (main phase A) and the lithium magnesium sodium silicate was added and mixed until no more fisheyes were observed. Then the mixture was heated to 50 degrees Celsius while the sodium chloride was added to the solution with moderate agitation. The resulting solution was mixed for 20 minutes. The VP/VA copolymer was added in small amounts, allowed to dissolve, and repeated until all of the VP/VA copolymer was used up. The solution was stirred until a uniform solution formed. The resulting mixture was heated to 80-85 degrees Celsius while continuously mixing. In a separate side phase B, the propylene glycol, methylparaben, and phenoxyethanol were combined and stirred until all solids in solution dissolved. Side phase B was then added to main phase A. In a second separate side phase C, the glyceryl stearate & PEG-100 stearate, cetearyl alcohol, beeswax, and cetyl esters were combined. The contents were then heated to 80-85 degrees Celsius to melt the wax and further mixed until enough of the waxes had melted. Once all of the waxes had melted, phase C was added to the main phase and mixed for 30 minutes. Once the time had elapsed, the triethanolamine was added to the solution and mixed until uniform. In a third separate side phase D, the C12-15 alkyl benzoate was placed in a beaker and the acrylates/C10-30 alkyl acrylate crosspolymer was slowly added while mixing until the resulting solution became homogeneous. Phase D was then added to the main phase. The batch was cooled to 60 degrees Celsius and mixed until the final batch became uniform.

Then, the mixture was allowed to cool down to room temperature.

Penetrometry Study

The texture of a composition can be characterized according its elastic behavior as measured by penetrometry. Using this method, the elastic behavior of a composition can be shown from its ability to store energy under a controlled deformation; that is, a normal exerted force by the composition does not become equal to zero over time. On the other hand, the normal exerted force by an inelastic material becomes equal to zero over time (also indicates a substantial lack of resistance to the probe).

Texture analysis of the inventive composition of the example above was measured using a Texture Analyzer TA.XT.$^{plus}$ from Stable Micro System (maximum detectable strength for the head of 50N). A controlled penetration (1 mm/s) into samples of the inventive composition was performed using a metal rod equipped with a P/20 aluminum cylinder probe (diameter=20 mm) at the head. The strength (resistance described as normal strength or normal exerted force) exerted by the inventive composition against the head over a ten minute period was measured.

FIG. 1 shows the curves of the normal strength (force in grams) exerted against the probe versus time (in seconds) for two sets of measurements conducted on a 6 mm sample of the composition above.

The curves revealed the elastic behavior of the inventive composition from the stored energy under deformation since the normal exerted force (normal strength) did not become equal to zero over time. The curves also revealed a minimum resistance to deformation of about 100 g of force after 10 minutes.

Evaluation of the Properties of the Inventive Composition on Hair

Two separate evaluation tests were conducted on the hair of twenty-six panelists with short to very short hair. Expert stylist evaluators trained to analyze the effects of cosmetic products applied onto hair conducted the tests.

Randomized half-head studies with the test compositions blinded were conducted, in which the inventive composition was applied by the expert stylist evaluator to either the left or right side of the panelists' head, and a commercial styling product was applied to the other side of the head. In first test involving 12 panelists, the composition was evaluated on dry hair for the properties of resurfacing or coating the hair with a mattifying effect and adding texture to the hair.

The inventive composition used in the first test had the following composition:

| Ingredients | % by weight |
|---|---|
| Lithium magnesium sodium silicate | 2.25 |
| Sodium chloride | 0.02 |
| vinylpyrrolidone/vinyl acetate copolymer | 2.00 |
| Propylene glycol | 3.00 |
| Methylparaben | 0.30 |
| Phenoxyethanol | 0.70 |
| Glyceryl stearate and PEG-100 stearate | 3.75 |
| Cetearyl alcohol | 3.75 |
| Beeswax | 1.75 |
| Cetyl esters | 1.50 |
| Triethanolamine | 0.40 |
| C12-15 alkyl benzoate | 3.20 |
| Acrylates/C10-30 alkyl acrylate crosspolymer | 0.40 |
| Iron oxides, colorants | 0.739 |
| Fragrance | 0.30 |
| Deionized Water | Q.S. to 100 |

In the second test involving 14 panelists, the composition was applied on freshly shampooed and towel dried hair and evaluated for the same properties as in the first test, in comparison to the same commercial styling product.

The inventive composition used in the second test had the following composition:

| Ingredients | % by weight |
|---|---|
| Lithium magnesium sodium silicate | 2.25 |
| Sodium chloride | 0.02 |
| vinylpyrrolidone/vinyl acetate copolymer | 2.00 |
| Propylene glycol | 3.00 |
| Methylparaben | 0.30 |
| Phenoxyethanol | 0.70 |
| Glyceryl stearate and PEG-100 stearate | 4.00 |
| Cetearyl alcohol | 4.00 |
| Beeswax | 1.75 |
| Cetyl esters | 1.50 |

-continued

| Ingredients | % by weight |
| --- | --- |
| Triethanolamine | 0.75 |
| C12-15 alkyl benzoate | 3.20 |
| Acrylates/C10-30 alkyl acrylate crosspolymer | 0.80 |
| Iron Oxides | 0.01 |
| Polyethylene Terephthalate and polyurethane and aluminum powder (Glitter powder) | 0.1 |
| Deionized Water | Q.S. to 100 |

The commercial styling product used for the comparison contained the following ingredients (as indicated on the product packaging): Aqua/Water, Cera Alba/Beeswax, PEG-100 Stearate, Glyceryl Stearate, Cetearyl Alcohol, Phenoxyethanol, PEG-150/Stearyl Alcohol/SMDI Copolymer, PPG-1-Trideceth-6, PEG-192 Apricot Kernel Glycerides, PEG-70 Mango Glycerides, Polyquaternium-37, Limonene, Linalool, Propylene Glycol Dicaprylate/Dicaprate, Propylene Glycol, Caramel, Butylparaben, Methylparaben, Citral, Citrus Limonum/Lemon Extract, Amyl Cinnamal, Partum/Fragrance.

In both tests, the inventive composition was found to have better properties compared to the commercial product in terms of mattifying effect and medium styling hold control with little to no crunch, adding volume and root lift with average suppleness and imparting to the hair added surface texture, a style memory and the ability to be repositioned or re-styled.

The invention claimed is:

1. A cosmetic composition comprising:
   (a) at least one silicate clay which is lithium magnesium sodium silicate, wherein the at least one silicate clay is present in an amount of from 1.0% to 5% by weight, based on the total weight of the composition;
   (b) at least one polymeric rheology modifier, wherein the at least one polymeric rheology modifier is acrylates/C10-30 alkyl acrylates crosspolymer, and wherein the at least one polymeric rheology modifier is present in an amount of from 0.3% to 0.8% by weight, based on the total weight of the composition;
   (c) at least one solvent which is water and an organic solvent comprising C12-C15 alkyl benzoates; and
   (d) at least one wax selected from the group consisting of animal waxes, vegetable waxes, mineral waxes, natural waxes, synthetic waxes, petroleum waxes, ethylenic polymers, hydrocarbons, silicone waxes, alkyl esters and mixtures thereof; and wherein the at least one wax is a solid at room temperature.

2. The composition of claim 1, wherein the at least one wax is present in an amount ranging from 0.1% to 10% by weight, based on the total weight of the composition.

3. The composition of claim 2, wherein the amount of wax ranges from 1% to 5% by weight, based on the total weight of the composition.

4. The composition of claim 1, further comprising at least one fixative polymer chosen from anionic, cationic, amphoteric and non-ionic fixative polymers and mixtures thereof, in an amount ranging from 0.05% to 15% by weight.

5. The composition of claim 4, wherein the amount of fixative polymer ranges from 1% to 5% by weight, based on the total weight of the composition.

6. The composition of claim 4, wherein the amount of fixative polymer ranges from 2% to 3% by weight, based on the total weight of the composition.

7. The composition of claim 4, wherein the at least one fixative polymer is chosen from polyvinylpyrrolidone, vinylpyrrolidone/vinyl acetate copolymers, acrylates/vinylpyrrolidone copolymers, polyquaternium-4, polyquaternium-6, polyquaternium-7, polyquaternium-10, polyquaternium-11, polyquaternium-16, polyquaternium-22, polyquaternium-28, polyquaternium-32, guar hydroxypropyltrimonium chloride, and mixtures thereof.

8. The composition of claim 1, wherein such composition has an elastic behavior.

9. A process for treating keratinous materials by applying onto said keratinous material a composition comprising:
   (a) at least one silicate clay which is lithium magnesium sodium silicate, wherein the at least one silicate clay is present in an amount of from 1.0% to 5% by weight, based on the total weight of the composition;
   (b) at least one polymeric rheology modifier, wherein the at least one polymeric rheology modifier is acrylates/C10-30 alkyl acrylates crosspolymer, and wherein the at least one polymeric rheology modifier is present in an amount of from 0.3% to 0.8% by weight, based on the total weight of the composition;
   (c) at least one solvent which is water and an organic solvent comprising C12-C15 alkyl benzoates; and
   (d) at least one wax selected from the group consisting of animal waxes, vegetable waxes, mineral waxes, natural waxes, synthetic waxes, petroleum waxes, ethylenic polymers, hydrocarbons, silicone waxes, alkyl esters and mixtures thereof; and wherein the at least one wax is a solid at room temperature.

10. The process of claim 9, wherein the keratinous material is the hair.

11. The process of claim 9, wherein the at least one wax is present in an amount ranging from 0.1% to 10% by weight, based on the total weight of the composition.

12. The process of claim 11, wherein the amount of wax ranges from 1% to 5% by weight, based on the total weight of the composition.

13. The process of claim 9, wherein the composition further comprises at least one fixative polymer chosen from anionic, cationic, amphoteric and non-ionic fixative polymers and mixtures thereof, in an amount ranging from 0.05% to 15% by weight.

14. The process of claim 13, wherein the amount of fixative polymer ranges from 1% to 5% by weight, based on the total weight of the composition.

15. The process of claim 13, wherein the amount of fixative polymer ranges from 2% to 3% by weight, based on the total weight of the composition.

16. The process of claim 13, wherein the at least one fixative polymer is chosen from polyvinylpyrrolidone, vinylpyrrolidone/vinyl acetate copolymers, acrylates/vinylpyrrolidone copolymers, polyquaternium-4, polyquaternium-6, polyquaternium-7, polyquaternium-10, polyquaternium-11, polyquaternium-16, polyquaternium-22, polyquaternium-28, polyquaternium-32, guar hydroxypropyltrimonium chloride, and mixtures thereof.

17. A method for styling and/or fixing the hair, comprising the step of applying onto the hair a composition comprising:
   (a) at least one silicate clay which is lithium magnesium sodium silicate, wherein the at least one silicate clay is present in an amount of from 1.0 to 5% by weight, based on the total weight of the composition;
   (b) at least one polymeric rheology modifier, wherein the at least one polymeric rheology modifier is acrylates/C10-30 alkyl acrylates crosspolymer, and wherein the at least one polymeric rheology modifier is present in an amount of from 0.3% to 0.8% by weight, based on the total weight of the composition;

(c) at least one solvent which is water and an organic solvent comprising C12-C15 alkyl benzoates; and
(d) at least one wax selected from the group consisting of animal waxes, vegetable waxes, mineral waxes, natural waxes, synthetic waxes, petroleum waxes, ethylenic polymers, hydrocarbons, silicone waxes, alkyl esters and mixtures thereof; and wherein the at least one wax is a solid at room temperature.

* * * * *